United States Patent
De Rooij

(12) 
(10) Patent No.: US 6,245,244 B1
(45) Date of Patent: *Jun. 12, 2001

(54) METHOD AND KIT FOR SEPARATING PLASMA FROM WHOLE BLOOD

(75) Inventor: Felix Wilhelmus Marie De Rooij, Gouda (NL)

(73) Assignee: Micro Diagnostic Innovations Nederland B.V., Gouda (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,790

(22) PCT Filed: Feb. 10, 1997

(86) PCT No.: PCT/NL97/00046

§ 371 Date: Sep. 1, 1998

§ 102(e) Date: Sep. 1, 1998

(87) PCT Pub. No.: WO97/29369

PCT Pub. Date: Aug. 14, 1997

(30) Foreign Application Priority Data

Feb. 9, 1996 (NL) .................................................. 1002296

(51) Int. Cl.[7] .................................................. B01D 37/00
(52) U.S. Cl. .................. 210/808; 210/406; 210/435; 210/505; 210/645; 210/767; 422/55; 422/101; 436/177
(58) Field of Search ................................ 210/406, 416.1, 210/435, 436, 503, 505, 508, 509, 645, 650, 651, 767, 808; 422/101, 61, 55, 58; 436/177, 178

(56) References Cited

U.S. PATENT DOCUMENTS

| | | |
|---|---|---|
| 4,263,922 | 4/1981 | White . |
| 4,632,901 * | 12/1986 | Valkirs et al. ........................ 422/61 |
| 4,874,691 * | 10/1989 | Chandler .............................. 422/61 |
| 5,064,541 * | 11/1991 | Jeng et al. ........................... 210/767 |
| 5,135,719 * | 8/1992 | Hillman et al. ...................... 210/503 |
| 5,147,780 * | 9/1992 | Pouletty et al. ...................... 422/61 |
| 5,362,654 * | 11/1994 | Pouletty ............................... 422/61 |
| 5,364,533 * | 11/1994 | Ogura et al. ........................ 210/505 |
| 5,589,399 * | 12/1996 | Allen et al. ......................... 436/177 |
| 5,725,774 * | 3/1998 | Neyer .................................. 210/505 |

FOREIGN PATENT DOCUMENTS

| | | |
|---|---|---|
| 849898 | 6/1977 | (BE) . |
| 0 439 917 | 8/1991 | (EP) . |
| 0 550 950 | 7/1993 | (EP) . |
| 2 335 267 | 7/1977 | (FR) . |
| 2 232 599 | 12/1990 | (GB) . |

* cited by examiner

*Primary Examiner*—Joseph W. Drodge
(74) *Attorney, Agent, or Firm*—Young & Thompson

(57) ABSTRACT

A method and kit for separating plasma from small quantities of whole blood. A mixture of less than 100 μl of whole blood, a blood anticoagulant and a diluent, is formed in a container provided with a sealing cap. The mixture is forced through a filter containing glass fibers by applying sub-atmospheric pressure to a side of the filter opposite the mixture. The method can be performed in a hypodermic syringe, or in a capillary.

13 Claims, No Drawings

METHOD AND KIT FOR SEPARATING PLASMA FROM WHOLE BLOOD

The invention relates to a method for separating plasma from whole blood. in which:
  a) a mixture of whole blood, a blood anticoagulant and a diluent is prepared in a container provided with a sealing cap, and
  b) the mixture obtained under a) is passed through a filter containing glass fibres.

Belgian Patent Application 849,898 describes a device for diluting and filtering a sample having a very small volume, such as, for example, a blood sample. Said device comprises a container which is made of a flexible plastic material and which contains a liquid diluent for the sample to be treated. The container is furthermore provided with a hollow cylindrical neck whose extremity is sealed with a removable stopper, and a cylindrical tube made of a flexible plastic material. The internal diameter of the cylindrical tube is essentially equal to the external diameter of the neck. The extremity of the cylindrical tube is inserted into a nozzle or fixed on a filter, the nozzle being sealed by a cannula. The container may optionally contain a capillary which contains a measured quantity of the sample, for example a blood sample. To dilute and filter, for example, a blood sample, the procedure is as follows. First the stopper is removed and the blood sample is transferred to the container either by means of the capillary or directly with the aid of an hypodermic syringe. The cylindrical tube is then mounted on the neck of the container and the device is shaken in such a way that a homogeneous mixture of the blood sample and the diluent is obtained, care being taken to ensure that the filter is not moistened. The homogeneous mixture is then filtered by squeezing the container, in which process the homogeneous mixture passes through the filter and a filtrate is obtained which has the desired dilution. A disadvantage of said device is that it is unsuitable for separating plasma from quantities of whole blood of, for example, less than 100 µl because the yield of pure plasma is low when such a small quantity of whole blood is separated. A further disadvantage of the device according to Belgian Patent Application 848,898 is that a large dilution has to be used in order to obtain an adequate volume of the homogeneous mixture: the volumetric ratio of the diluent and the blood sample should be between 10:1 and 1000:1. After dilution and filtering, therefore, a very dilute plasma will be obtained, as a result of which only diagnostic tests having a low sensitivity can be carried out.

In medical diagnostics, the separation of plasma from whole blood is extremely important for analysing constituents present in the blood. Such analyses often take place with the aid of rapid diagnostic means. Rapid diagnostic means are, for example, substrates which comprise a separating matrix for separating plasma from whole blood and a test reagent. In this procedure, a drop of whole blood is applied to the substrate, clear plasma passing through the separating matrix and the blood corpuscles, such as erythrocytes and leucocytes, remaining behind in the matrix. The plasma then reacts with the test reagent, in which process a colour change occurs which is then evaluated visually or spectrophotometrically. A disadvantage of said rapid diagnostic means is that haemolysis of erythrocytes may occur, in which process haemoglobin is entrained with the plasma and may interfere with the colour reaction.

These problems do not occur, for example, in the case of rapid diagnostic means in which plasma containing no haemolysis products is applied instead of whole blood. In this case, the plasma first has to be separated from the whole blood by means of centrifuging, after which the plasma can be separated from the blood corpuscles deposited by means of pipetting. The separation of plasma from whole blood by this method is not easy if it has to be carried out on a small scale. This is primarily of importance in the case of, for example. children, where the taking of a small amount of blood by means of a heel or finger prick results in far fewer problems with the patients than if blood is collected with the small vacuum tubes normally used. A small vacuum tube is a small tube which has a capacity of approximately 7 to 10 ml, which is provided with a stopper made, for example, of rubber and which has to be fitted on an injection needle after the injection needle has been introduced into a vein, for example a vein in the arm (venepuncture). Because a lower pressure prevails in the small vacuum tube than in the vein, blood will flow out of the vein into the small vacuum tube.

Another disadvantage of the method described above is that the separation of the plasma has to be carried out by expert staff or by staff specially trained for the purpose and that special equipment is required. It is therefore not possible to collect whole blood and to separate the plasma therefrom at the same operational site. This is of importance, for example, under circumstances in which urgent help has to be offered and one or more diagnostic tests have to be carried out and special equipment is not available. Thus, for example, a general practitioner or a medical specialist will possibly consider it necessary, when visiting patients at home or in cases where acute help is needed, respectively, to carry out a certain test but will not be in a position to extract the required amount of plasma rapidly and expediently. Another example is the evaluation of new diagnostic blood parameters for which no specific whole blood tests are generally available for a long time. Only small amounts of blood are also necessary for many diagnostic tests, for example tests for the determination of the concentration of a metabolite, a hormone or an antibody. Furthermore, for example, veterinary surgeons cannot obtain an amount of plasma for a certain diagnostic test from an animal in its own living environment, for example a cow in its shed.

U.S. Pat. No. 4,477,575 describes a method for separating plasma from whole blood in which whole blood is applied to a layer of glass fibres. A device is also described for separating plasma from whole blood, the device comprising a conical plastic vessel, the top and bottom of the vessel being open. The lowermost part of the vessel is filled with glass fibres. The blood is then introduced into the free section of the vessel, after which plasma flows through the layer comprising the glass fibres and can be removed at the bottom with the aid of a capillary. U.S. Pat. No. 5,262,067 describes a device for separating plasma from whole blood, in which little haemolysis occurs and in which the device comprises a layer comprising glass fibres coated with polyvinyl alcohol or polyvinyl alcohol/polyvinyl acetate, and a means which causes erythrocytes to aggregate. If an amount of whole blood is applied to the top of the layer, erythrocytes are aggregated and plasma containing little or no haemolysis products passes through the layer. This method and device have, however, the disadvantage that they are unsuitable for expediently separating and isolating plasma from small amounts of whole blood so that said plasma can be used for other diagnostic tests.

The object of the invention is to solve the abovementioned problems and it therefore relates to a method as stated in the preamble, in which a pressure which is lower than the pressure prevailing at ambient temperature prevails in the container. The invention also relates to a kit for separating plasma from whole blood.

Advantages of the method according to the invention are that the method is particularly suitable for separating plasma from small amounts of whole blood, for example amounts of less than 100 µl. Such amounts can be collected by means of a heel or finger prick in a particularly patient-friendly manner. In addition, such amounts are in many cases quite sufficient for many diagnostic tests, for example tests for determining the concentration of a metabolite, a hormone or an antibody in blood.

For the heel or finger prick, a capillary is advantageously used which comprises a container provided with, for example, a small elliptical needle having a length of less than 1.5 mm.

A further advantage of the invention is that plasmas is obtained from the whole blood in a particularly expedient manner and with a very high yield. Other advantages of the invention are that no special equipment is necessary, so that the separation of plasma from whole blood can be carried out at the site where the patient is. This last advantage may be of particular importance, for example, for doctors who have to treat patients on the spot and in circumstances already described above. A further advantage is that non-specialists can also separate plasma from whole blood by the method of the invention. In addition, plasma is obtained which only has to be diluted slightly before it is separated from the whole blood. It has been found that a dilution of 100% is adequate, that is to say that the volumetric ratio of plasma to diluent is no higher than 1:5, preferably no higher than 1:3 and in particular no higher than 1:2. According to the method of the present invention, it is possible to obtain only slightly diluted plasma which is very suitable for carrying out diagnostic tests in which a high sensitivity is desirable.

According to the invention, the preparation of the mixture of whole blood, the blood anticoagulant and the diluent is carried out in a hypodermic syringe having a volume of, for example, 1 ml. In this process, the mixture of whole blood and blood anticoagulant is preferably prepared first, after which said mixture is then mixed with the diluent.

According to the invention, the blood anticoagulant is preferably heparin. The diluent may be any buffer solution which is necessary for the desired diagnostic test. An example of such a diluent is a phosphate buffer which contains 0.1% by weight of sodium azide and has a pH of approximately 7.2. The diluent may also contain one or more standard surface-active agents, preferably non-ionic surface-active agents. The diluent may also contain other agents necessary for a particular diagnostic test.

According to the invention, the mixture of whole blood and blood anticoagulant is preferably prepared in a capillary which is suitable for collecting a small amount of blood by means of a heel or finger prick and which contains the blood anticoagulant. The mixture of whole blood and blood anticoagulant is then removed with the aid of the hypodermic syringe in which an amount of the diluent has been taken up beforehand. Although it is not preferable according to the invention, it will be clear that it is optionally possible to remove the mixture of whole blood and blood anticoagulant first from the capillary using the hypodermic syringe and then to draw up a certain amount of the diluent with the aid of the hypodermic syringe. According to the invention, it is also preferable that a long and thin hypodermic syringe is used, for example a hypodermic syringe having a length of approximately 7 to approximately 10 cm and a diameter of approximately 3 to approximately 9 mm. Suitable hypodermic syringes are, for example, those which have a volume of 3 ml of the type Sherwood Monoject which are provided with a "Luer lock" (reference No. 1100-503497).

Preferably a hypodermic syringe is used which has been filled with the diluent and an amount of a gas, a pressure below the ambient pressure, preferably a pressure between 1 and 0.5 bar, prevailing in the hypodermic syringe at ambient temperature, which syringe has been provided with a sealing cap. According to the invention, the pressure in the hypodermic syringe at ambient temperature is, in particular, at least 0.5 bar. the hypodermic syringe having a volume of 1 ml and the plunger of the hypodermic syringe being in the fully extended state.

The sealing cap can be pierced by a capillary and is and remains, even after piercing, essentially impermeable to gases. Examples of such sealing caps are septa and ferrules. According to the invention, the sealing caps are preferably made of a material which does not interact with whole blood, the diluent and the gas. The sealing caps are preferably made of an inert plastic material or are coated on the inside with an inert plastic material. A suitable inert plastic material is, for example, Teflon.

The hypodermic syringe may be provided with an internal pressure of 0.5 bar by filling it, for example, with a gas having a temperature which is higher than the ambient temperature. After cooling the gas to ambient temperature, a pressure which is lower than the ambient pressure will then be produced in the hypodermic syringe. If the sealing cap is then pricked with the capillary containing the mixture of whole blood and blood anticoagulant, the contents of the capillary will be drawn into the hypodermic syringe.

It will be clear that the hypodermic syringe is filled with a gas which does not interact with the whole blood or a constituent thereof, the blood anticoagulant or the diluent. Examples of suitable gases are nitrogen, oxygen or air.

The mixture containing whole blood. the blood anticoagulant and the diluent is introduced into the hypodermic syringe, whose plunger is already in the completely extended state. To obtain a good mixing, the hypodermic syringe may, if necessary, be rotated horizontally and vertically. The hypodermic syringe may also contain media which promote mixing, for example glass beads, so that mixing can be carried out more expediently. The sealing cap is removed and the hypodermic syringe is then connected to a container which contains the filter comprising glass fibres. The liquid is transferred to the filter by tapping the hypodermic syringe and, after a means of locking the plunger has been broken, preferably by rotating, the contents of the hypodermic syringe are then forced through the filter with the aid of the plunger, a filtrate being obtained in the form of drops which comprises the plasma and contains no haemolysis products.

According to the invention, although partly dependent on the diluent used, drops of plasma are obtained which have a more or less uniform volume. This is achieved by matching the amount and the nature of the surface-active agent used to the properties of the diluent, such as, for example, the pH, the salt concentration and the like.

A great advantage of the method described above is that a kit can be assembled which is suitable for separating a certain amount of plasma which is necessary for the desired diagnostic test. The invention therefore also relates to a kit which comprises at least a container which contains an amount of a diluent necessary for a certain diagnostic test, and a filter containing glass fibres, a pressure prevailing in the container which is lower than the pressure prevailing at ambient temperature. The kit may also contain a capillary which contains an amount of blood anticoagulant necessary for the blood to be collected. The container has a volume which is such that it can contain the amount of whole blood, blood anticoagulant and diluent and, if necessary gas, a pressure of at least 0.5 bar prevailing in the hypodermic syringe at ambient temperature.

According to the invention, it is also possible for the kit as defined hereinabove to comprise a hypodermic syringe which comprises the container containing diluent or the diluent alone. Preferably, the kit also contains at least one diagnostic test which can be carried out with a small amount of plasma, for example with 40 µl of plasma.

Although the blood anticoagulant be contained in the diluent contained in the container may instead of in the capillary, this is generally not to be preferred according to the invention because blood corpuscles may already adhere to the glass wall of the capillary. The kit according to the invention may also contain one or more means necessary for carrying out a certain diagnostic test. Examples of such means are test strips for determining the presence of a certain concentration of metabolite, hormone or antibody in the blood and the reagents necessary therefor.

The invention also relates to a device. A preferred embodiment comprises a hypodermic syringe which is provided with a plunger and means for locking the plunger and which optionally contains media which promote mixing, such as glass beads, a nozzle and a sealing cap for sealing the nozzle, a pressure of at least 0.5 bar prevailing in the hypodermic syringe at ambient temperature. It goes without saying that the hypodermic syringe may be replaced by another suitable container.

The means of locking the plunger have to be present because, if the said means were not present this underpressure would become lower or even be completely eliminated by moving the plunger. The unlocking of the means preferably takes place by means of rotation.

The nozzle of the hypodermic syringe is preferably provided with a common screw thread, for example a "Luer lock" so that the hypodermic syringe can be connected in a simple manner to the container which contains the filter comprising glass fibres. Instead of a screw thread, another means may also be present for connecting the hypodermic syringe to the holder containing the filter.

The nozzle is also provided with a sealing cap. Said sealing cap may partly or in its entirety be composed of a material which can be pierced by a capillary. The material is also essentially impermeable to gases and also remains impermeable to gases if the material has been pierced several times with a capillary. Examples of such materials are plastic materials, preferably elastic inert plastic materials and, in particular, rubber-like materials. Examples of suitable sealing caps are septa and ferrules.

The invention will now be explained by reference to an example.

EXAMPLE 1

An amount of 75 $\mu$l of whole blood is collected by a finger prick with the aid of a commercially available capillary containing the standard amount of heparin. This amount of heparin is generally quite sufficient to inhibit the coagulation of the amount of whole blood collected. The whole blood has a haematocrit reading of 0.40 and therefore consists of 45 $\mu$l of plasma and 30 $\mu$l of blood cells.

An amount of 135 $\mu$l of a phosphate buffer having a pH of 7.2 is drawn up with the aid of a hypodermic syringe having a volume of 1 ml. The mixture of whole blood and heparin is then removed from the capillary with the aid of the hypodermic syringe and the plunger is pulled out to a volume of 1 ml.

A filter which comprises glass fibres and has a dead volume of 38 $\mu$l is then mounted on the nozzle of the hypodermic syringe. The hypodermic syringe, which is now provided with the filter, is rotated several times horizontally and vertically to obtain a good mixing of all the constituents. The mixture is transferred to the filter by lightly tapping the hypodermic syringe. The plunger is then carefully pressed in, and three completely clear, colourless drops each having a volume of approximately 40 $\mu$l are obtained as filtrate. The yield of plasma is therefore 85%.

EXAMPLE 2

The test of Example 1 was repeated, with the proviso that a pressure of approximately 0.6 bar prevailed in the hypodermic syringe and, at the same time, the hypodermic syringe was provided with a means for locking the plunger. In this test three completely clear, colourless drops were also obtained which had a total volume of approximately 120 $\mu$l.

What is claimed is:

1. A method for separating plasma from small quantities of whole blood, comprising forming a mixture of a blood coagulant and a diluent and less than 100 $\mu$l of whole blood in a container provided with a sealing cap, the pressure prevailing in said container being below atmospheric pressure, and forcing said mixture from said container through a filter containing glass fibers by applying pressure to said mixture.

2. A method as claimed in claim 1, wherein said container is a syringe having a movable plunger by which said mixture is forced through said filter.

3. A method as claimed in claim 1, wherein said diluent contains a non-ionic surfactant.

4. A method as claimed in claim 3, wherein a mixture of said blood anticoagulant and whole blood is formed in a capillary, and is then transferred to said container by penetration of said sealing cap by said capillary.

5. A method as claimed in claim 3, wherein said container is connected to a second container containing the filter before the mixture is passed through the filter.

6. A kit constructed and arranged for separating plasma from a sample of whole blood of less than 100 $\mu$according to the method of claim 1, which comprises at least a container containing a diluent and a filter containing glass fibers, the kit being constructed and arranged such that pressure prevailing in the container before a sample is drawn into the container is lower than atmospheric pressure.

7. A kit as claimed in claim 6, wherein said container is a syringe having a movable plunger by which said whole blood and diluent can be ejected from said container.

8. A kit as claimed in claim 6, which also contains a capillary for containing a blood anticoagulant.

9. A kit as claimed in claim 6, also containing at least one means for performing a diagnostic test.

10. A method for separating plasma from small quantities of whole blood, comprising collecting less than 100 $\mu$l of whole blood in a capillary containing a blood anticoagulant, and transferring the whole blood and anticoagulant to a container provided with a sealing cap, said container containing a diluent and the pressure prevailing in said container being below atmospheric pressure, the transfer from the capillary being effected by the sub-atmospheric pressure prevailing in said container, thereby to form a mixture of blood anticoagulant and diluent and less than 100 $\mu$l of whole blood in said container, and thereafter forcing said mixture through a filter containing glass fibers by applying pressure to said mixture.

11. A method as claimed in claim 10, wherein the container is a syringe having a movable plunger by which said mixture can be ejected from said syringe.

12. A method as claimed in claim 10, wherein said diluent contains a non-ionic surfactant.

13. A method as claimed in claim 10 wherein said container is first connected to a second container containing the filter before the mixture is passed through the filter.

* * * * *